US 6,720,316 B2

(12) United States Patent
McWhorter, Jr.

(10) Patent No.: US 6,720,316 B2
(45) Date of Patent: Apr. 13, 2004

(54) THERAPEUTIC 5-HT LIGAND COMPOUNDS

(75) Inventor: William W. McWhorter, Jr., Parchment, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/211,879

(22) Filed: Aug. 2, 2002

(65) Prior Publication Data

US 2003/0050300 A1 Mar. 13, 2003

Related U.S. Application Data

(60) Provisional application No. 60/310,331, filed on Aug. 6, 2001.

(51) Int. Cl.$^7$ .................... C07D 491/18; C07D 513/18; A61K 31/54; A61K 31/5386
(52) U.S. Cl. .................... 514/215; 544/14; 544/99; 540/477; 540/578; 514/224.5; 514/229.5
(58) Field of Search .................... 544/14, 99; 540/477, 540/578; 514/215, 224.5, 229.5

(56) References Cited

U.S. PATENT DOCUMENTS

| 4,219,550 A | 8/1980 | Rajagopalan ............... 424/246 |
| 4,438,120 A | 3/1984 | Rajagopalan ............... 424/256 |

FOREIGN PATENT DOCUMENTS

| WO | WO 00/77001 | 12/2000 |
| WO | WO 00/77002 | 12/2000 |
| WO | WO 00/77010 | 12/2000 |

*Primary Examiner*—Mark L. Berch
*Assistant Examiner*—Kahsay Habte
(74) *Attorney, Agent, or Firm*—Flynn, Thiel, Boutell & Tanis, P.C.

(57) ABSTRACT

The present invention provides compounds of Formula (I)

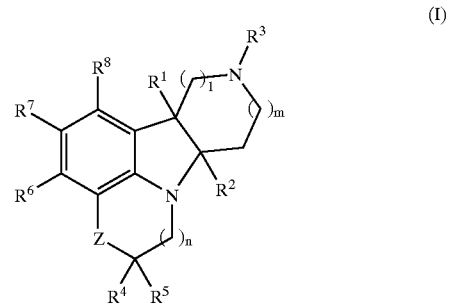

(I)

wherein $R^1$, $R^2$, $R^3$, $R^4$, $R^5$, $R^6$, $R^7$, $R^8$ and Z have any of the values defined in the specification, as well as pharmaceutical compositions comprising the compounds. The invention also provides therapeutic methods as well as processes and intermediates useful for preparing compounds of Formula (I). The compounds are 5-HT ligands, and are useful for treating diseases whereas modulation of 5-HT activity is desired.

40 Claims, No Drawings

THERAPEUTIC 5-HT LIGAND COMPOUNDS

CROSS REFERENCE TO RELATED APPLICATIONS

This application claims the benefit of U.S. provisional application Ser. No. 60/310331 filed on Aug. 6, 2001, under 35 USC 119(e)(i), which is incorporated herein by reference in its entirety.

FIELD OF THE INVENTION

The present invention provides tricyclic hexahydroazepinoindole and indoline derivatives, and more specifically, provides compounds of Formula (I) described hereinbelow. These compounds are 5-HT ligands, and are useful for treating diseases wherein modulation of 5-HT activity is desired.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, ed. Neville V. Osborne, John Wiley and Sons (1982), p 221; D. J. Boullin, Serotonin in Mental Abnormalities 1, John Wiley and Sons (1978), p. 316; J. Barchas, et al., Serotonin and Behavior, Academic Press, New York, N.Y. (1973). Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting. M. D. Gershon, et al., The Peripheral Actions of 5-Hydroxytryptamine, 246 (1989); P. R. Saxena, et al., Journal of Cardiovascular Pharmacology, 15:Supplement 7 (1990).

The major classes of serotonin receptors (5-HT$_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203. Recently discovered information regarding subtype identity, distribution, structure, and function suggests that it is possible to identify novel, subtype specific agents, having improved therapeutic profiles (e.g. fewer side effects).

For example, the 5-HT$_2$ family of receptors is comprised of 5-HT$_{2A}$, 5-HT$_{2B}$, and 5-HT$_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three 5-HT$_2$ subtypes. The 5-HT$_{2B}$ and 5-HT$_{2A}$ receptors are widely distributed in the periphery, while the 5-HT$_{2C}$ receptor has been found only in the central nervous system, being highly expressed in many regions of the human brain. See G. Baxter, et al. Trends in Pharmacol. Sci. 1995, 16, 105–110.

Subtype 5-HT$_{2A}$ has been associated with effects including vasoconstriction, platelet aggregation, and bronchoconstriction, while subtype 5-HT$_{2C}$ has been associated with diseases that include depression, anxiety, obsessive compulsive disorder, panic disorders, phobias, psychiatric syndromes, and obesity. Very little is known about the pharmacological role of the 5-HT$_{2B}$ receptor. See F. Jenck, et al., Exp. Opin. Invest. Drugs, 1998, 7, 1587–1599; M. Bos, et al., J. Med. Chem., 1997, 40, 2762–2769; J. R. Martin, et al., The Journal of Pharmacology and Experimental Therapeutics, 1998, 286, 913–924; S. M. Bromidge, et al., J. Med. Chem., 1998, 41 1598–1612; G. A. Kennett, IDrugs, 1998, 1, 4, 456–470; and A. Dekeyne, et al., Neuropharmacology, 1999, 38, 415–423.

International Patent Applications WO 00/77001, WO 00/77002, and WO 00/77010 disclose tetracyclic compounds that are reported to possess activity as serotonin agonists and antagonists.

U.S. Pat. No. 4,438,120 discloses polycyclic compounds that are reported to possess tranquilizer activity.

U.S. Pat. No. 4,219,550 discloses tetracyclic compounds that are reported to possess tranquilizer and antidepressant properties.

There is currently a need for pharmaceutical agents that are useful to treat diseases and conditions that are associated with 5-HT receptors.

SUMMARY OF THE INVENTION

In accordance with the present invention, novel compounds which demonstrate useful biological activity, and particularly activity as 5-HT receptor ligands, are provided. Thus, the present invention provides a compound of Formula (I):

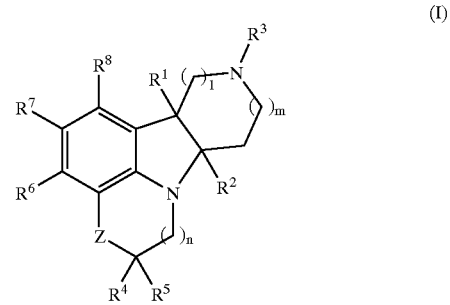

(I)

wherein Z is —CHR$^9$—, —C(O)—, —O—, —S—, —S(O)—, —SO$_2$—, —N(R$^9$)—, —C(O)N(R$^9$)—, or —N(R$^9$)C(O)—;

l is 1 or 2;

m is 0, 1 or 2;

n is 1 or 2;

R$^1$ is hydrogen, C$_{1-6}$alkyl, C$_{3-6}$cycloalkyl, or (C$_{3-6}$cycloalkyl)C$_{1-6}$alkyl; and R$^2$ is hydrogen, C$_{1-6}$alkyl, C$_{3-6}$cycloalkyl, or (C$_{3-6}$cycloalkyl)C$_{1-6}$alkyl; provided that R$^1$ and R$^2$ are not both hydrogen;

R$^3$ is hydrogen or C$_{1-6}$alkyl;

R$^4$, R$^5$ and R$^9$ are independently hydrogen, C$_{1-6}$alkyl or arylC$_{1-6}$alkylene;

R$^6$, R$^7$, and R$^8$ are independently hydrogen, fluoro, chloro, bromo, CF$_3$, —OCF$_3$, —N(R$^{10}$)$_2$, C$_{1-6}$alkyl, C$_{1-6}$alkoxy, heteroaryl or aryl; and each $R^{10}$ is independently hydrogen, or —$C_{1-6}$alkyl;

wherein any $C_{1-6}$alkyl, $C_{1-6}$alkylene, or $C_{1-6}$alkoxy of $R^1$, $R^2$, $R^3$, $R^4$, $R^5$, $R^6$, $R^7$, $R^8$, $R^9$, and $R^{10}$ is optionally partially unsaturated; and wherein any heteroaryl or aryl is optionally substituted with one or two halo, —$CF_3$, —$OCF_3$, $C_{1-6}$alkoxy, —$N(R^{10})_2$, or —$C_{1-6}$alkyl;

or a pharmaceutically acceptable salt thereof.

In another aspect, the present invention also provides:

a pharmaceutical composition comprising a compound of Formula (I), or a pharmaceutically acceptable salt thereof, and a pharmaceutically acceptable excipient (the composition preferably comprises a therapeutically effective amount of the compound or salt), a method for treating a disease or condition in a mammal (e.g. a human) in need thereof wherein a 5-HT receptor is implicated and modulation of a 5-HT function is desired comprising administering a therapeutically effective amount of a compound of Formula (I), or a pharmaceutically acceptable salt thereof to the mammal, a method for treating or preventing a disease or disorder of the central nervous system in a mammal in need thereof comprising administering a therapeutically effective amount of a compound of Formula (I), or a pharmaceutically acceptable salt thereof to the mammal, a compound of Formula (I) or a pharmaceutically acceptable salt thereof for use in medical diagnosis or therapy (e.g. the treatment or prevention of 5-HT related disease such as anxiety, obesity, depression, or a stress related disease), the use of a compound of Formula (I), or a pharmaceutically acceptable salt thereof to prepare a medicament useful for treating or preventing a disease or disorder of the central nervous system in a mammal in need thereof, and a method for modulating 5-HT receptor function, comprising administering an effective modulatory amount of a compound of Formula (I), or a pharmaceutically acceptable salt thereof.

The invention also provides novel intermediates of Formula II and processes disclosed herein that are useful for preparing compounds of Formula (I):

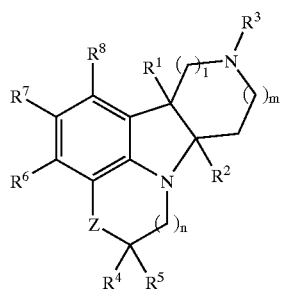

Formula II wherein $R^1$, $R^2$, $R^4$, $R^5$, $R^6$, $R^7$, $R^8$, l, m, and n, have the definitions of formula I and $R^3$ is —C(O)-aryl, —C(O)—heteroaryl, —C(O)—$C_{1-6}$alkyl, —C(O)—$C_{1-6}$haloalkyl, —C(O)O—$C_{1-6}$alkyl, or —C(O)O—$C_{1-6}$haloalkyl, where aryl or heteroaryl is optionally substituted with one or two halo, —$CF_3$, —$OCF_3$, $C_{1-6}$alkoxy, —$N(R^{10})_2$, or —$C_{1-6}$alkyl.

DETAILED DESCRIPTION OF THE INVENTION

The compounds of the invention are useful for treating or preventing diseases or disorders of the central nervous system. Specific diseases or disorders of the central nervous system for which a compound of Formula (I) may have activity include, but are not limited to: obesity, depression, schizophrenia, schizophreniform disorder, schizoaffective disorder, delusional disorder, a stress related disease (e.g. general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine, headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific development disorder, agitation disorder, selective serotonin reuptake inhibition (SSRI) "poop out" syndrome or a Tic disorder (e.g., Tourette's syndrome).

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Alkylene denotes a divalent straight or branched alkyl (e.g. ethylene —$CH_2CH_2$—) . When alkyl or alkylene can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-8}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine 5-HT activity using the standard tests which are well known in the art.

The carbon atom content of various hydrocarbon-containing moieties is indicated by a prefix designating the minimum and maximum number of carbon atoms in the moiety, i.e., the prefix $C_{i\text{-}j}$ indicates a moiety of the integer "i" to the integer "j" carbon atoms, inclusive. Thus, for example, $C_{1\text{-}8}$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, $C_{1\text{-}6}$alkyl can be methyl, ethyl, propyl, isopropyl, butyl, iso-butyl, sec-butyl, pentyl, 3-pentyl, or hexyl; $C_{1\text{-}6}$alkoxy can be methoxy, ethoxy, propoxy, isopropoxy, butoxy, iso-butoxy, sec-butoxy, pentoxy, 3-pentoxy, or hexyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for Z is —CHR$^9$—, —C(O)—, —O—, —S—, —S(O)—, —SO$_2$—, or —N(R$^9$)—.

A specific value for Z is —CHR$^9$—, —C(O)—, —S—, or —O—.

A specific value for Z is —O—.

A specific value for R$^1$ is hydrogen.

A specific value for R$^1$ is $C_{1\text{-}6}$alkyl, $C_{3\text{-}6}$cycloalkyl, or ($C_{3\text{-}6}$cycloalkyl)$C_{1\text{-}6}$alkyl.

A specific value for R$^1$ is $C_{2\text{-}6}$alkyl, $C_{3\text{-}6}$cycloalkyl, or ($C_{3\text{-}6}$cycloalkyl)$C_{1\text{-}6}$alkyl.

A specific value for R$^1$ is $C_{3\text{-}6}$alkyl, $C_{3\text{-}6}$cycloalkyl, or ($C_{3\text{-}6}$cycloalkyl)$C_{1\text{-}6}$alkyl.

A specific value for R$^1$ is methyl, ethyl, propyl, isopropyl, or cyclopropylmethyl.

A specific value for R$^1$ is ethyl, propyl, isopropyl, or cyclopropylmethyl.

A specific value for R$^1$ is propyl, isopropyl, or cyclopropylmethyl.

A specific value for R$^1$ is ethyl or propyl.

A specific value for R$^1$ is $C_{2\text{-}3}$alkyl.

A specific value for R$^2$ is hydrogen.

A specific value for R$^2$ is $C_{1\text{-}6}$alkyl, $C_{3\text{-}6}$cycloalkyl, or ($C_{3\text{-}6}$cycloalkyl)$C_{1\text{-}6}$alkyl.

A specific value for R$^2$ is $C_{2\text{-}6}$alkyl, $C_{3\text{-}6}$cycloalkyl, or ($C_{3\text{-}6}$cycloalkyl)$C_{1\text{-}6}$alkyl.

A specific value for R$^2$ is $C_{3\text{-}6}$alkyl, $C_{3\text{-}6}$cycloalkyl, or ($C_{3\text{-}6}$cycloalkyl)$C_{1\text{-}6}$alkyl.

A specific value for R$^2$ is methyl, ethyl, propyl, isopropyl, or cyclopropylmethyl.

A specific value for R$^2$ is ethyl, propyl, isopropyl, or cyclopropylmethyl.

A specific value for R$^2$ is propyl, isopropyl, or cyclopropylmethyl.

A specific value for R$^2$ is ethyl, propyl or butyl.

A specific value for R$^2$ is arylC$_{1\text{-}8}$alkylene.

A specific value for R$^2$ is $C_{2\text{-}6}$alkyl.

A specific compound of Formula (I) is a compound wherein R$^1$ is hydrogen, and wherein R$^2$ has any of the specific or preferred valued described herein.

A specific value for R$^3$ is hydrogen.

A specific value for R$^3$ is $C_{1\text{-}6}$alkyl.

A specific value for R$^3$ is methyl, ethyl, propyl or butyl.

A more specific value for R$^3$ is methyl or ethyl.

A specific value for R$^4$ is hydrogen, methyl, ethyl, propyl, butyl, 2-phenylethyl or benzyl.

A specific value for R$^4$ is hydrogen, methyl, ethyl, propyl or benzyl.

A specific value for R$^4$ is methyl, ethyl or benzyl.

A specific value for R$^5$ is hydrogen, methyl, ethyl, propyl, butyl, 2-phenylethyl or benzyl.

A specific value for R$^5$ is hydrogen, methyl, ethyl, propyl or benzyl.

A specific value for R$^5$ is methyl, ethyl or benzyl.

A specific value for R$^6$, R$^7$, or R$^8$ is phenyl optionally substituted with one or two substituents independently selected from fluoro, chloro, bromo, —CF$_3$, —OCF$_3$, $C_{1\text{-}6}$alkoxy, —N(R$^{10}$)$_2$, and $C_{1\text{-}6}$alkyl.

A specific value for R$^6$ is phenyl optionally substituted with one or two substituents independently selected from fluoro, chloro, bromo, —CF$_3$, —OCF$_3$, $C_{1\text{-}6}$alkoxy, —N(R$^{10}$)$_2$, and $C_{1\text{-}6}$alkyl.

A specific value for R$^7$ is phenyl optionally substituted with one or two substituents independently selected from fluoro, chloro, bromo, —CF$_3$, —OCF$_3$, $C_{1\text{-}6}$alkoxy, —N(R$^{10}$)$_2$, and $C_{1\text{-}6}$alkyl.

A specific value for R$^8$ is phenyl optionally substituted with one or two substituents independently selected from fluoro, chloro, bromo, —CF$_3$, —OCF$_3$, $C_{1\text{-}6}$alkoxy, —N(R$^{10}$)$_2$, and $C_{1\text{-}6}$alkyl.

A specific value for R$^6$ is 2,4-dichlorophenyl or 2,6-difluorophenyl.

A specific value for R$^7$ is 2,4-dichlorophenyl or 2,6-difluorophenyl.

A specific value for R$^8$ is 2,4-dichlorophenyl or 2,6-difluorophenyl.

Another aspect of the present invention is where R$^1$ is H, and R$^2$ is alkyl. Another aspect of the present invention is where R$^1$ is alkyl, and R$^2$ is H. Another aspect of the present invention is where each R$^1$ and R$^2$ are alkyl.

Specifically, the invention also provides a method for treating or preventing anxiety, obesity, depression, schizophrenia, a stress related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human) in need thereof comprising administering a therapeutically effective amount of a compound of Formula (I), or a pharmaceutically acceptable salt thereof to the mammal.

Specifically, the invention also provides a method of treating or preventing anxiety, obesity, depression, or a stress related disease, comprising administering to a mammal (e.g. a human) in need of such treatment, a therapeutically effective amount of a compound of Formula (I) or a pharmaceutically acceptable salt thereof.

Specifically, the invention also provides the use of a compound of Formula (I) or a pharmaceutically acceptable salt thereof to prepare a medicament for treating or preventing anxiety, obesity, depression, schizophrenia, a stress related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human) in need thereof.

Specifically, the invention also provides the use of a compound of Formula (I) or a pharmaceutically acceptable salt thereof to prepare a medicament for treating or preventing anxiety, obesity, depression, or a stress related disease in a mammal (e.g. a human) in need thereof.

The invention also provides a method for preparing a compound of Formula (I) wherein $R^3$ is hydrogen comprising deprotecting a corresponding compound of Formula (I) wherein $R^3$ is a suitable nitrogen protecting group.

Compounds of the invention can generally be prepared using the synthetic methods illustrated in Scheme 1. Starting materials can be prepared by procedures described herein or by procedures that would be well known to one of ordinary skill in organic chemistry. The variables used in the Scheme are as defined below or as in the claims.

The secondary amino group of a suitably substituted 4-piperidone hydrochloride, monohydrate I-1 [J Hamon, F Espaze, J Vignon, J-M Kamenka, *Eur. J. Med. Chem.* 34 125–35 (1999)] is protected with an electron withdrawing protecting group, such as, for example, a trifluoroacetyl group, in the presence of a base, such as pyridine, in an appropriate solvent, such as $CH_2Cl_2$, at room temperature to yield I-2. AGM Barrett, JCA Lana, *J. Chem. Soc., Chem. Com.* 471 (1978). The N-protected 4-piperidone I-2 is reacted with a substituted hydrazine hydrochloride I-3 in an appropriate solvent, such as 2-propanol, at reflux to yield an intermediate N-alkylindolinine salt, which is in turn reacted with an appropriate nucleophile, such as hydride, derived from a reducing agent, such as $NaBH_4$, or a Grignard reagent, to yield indoline I-4. See for example A. Ebnoether, et al., *Helv. Chim. Acta* 52 629–38 (1969). The protecting group of the amino nitrogen is removed under appropriate conditions, such as, for example, treatment with a basic reagent, such as NaOH, in an appropriate solvent, such as 1:1 $THF:H_2O$, at room temperature. The amino nitrogen is reprotected with a protecting group, such as, for example, a tert-butoxy carbonyl group, in the presence of a base, such as, for example, NaOH, in an appropriate solvent, such as, for example, 1:1 $THF:H_2O$ to yield indoline I-5. Depending upon the nature of amino nitrogen protecting group, it may be unnecessary to carry out this protecting group (I4→I5) exchange. Indoline I-5 is halogenated with a halogenating agent, such as bromine, in an appropriate solvent, such as chloroform, to yield the halogenated indoline I-6. [See for example, the procedure in WO 0077010 A2] Indoline I-6 is coupled with an appropriate aryl boronic acid in the presence of an appropriate catalyst, such as dichlorobis (triphenylphosphine)-palladium (II), and an appropriate base, such as 2N $Na_2CO_3$, in an appropriate solvent, such as benzene, to yield indoline I-7. N Miyaura, A Suzuki, *Chem. Rev.* 95 2457–83 (1995). Other types of coupling reactions, such as the Stille reaction, may also be used to bring about formation of this aryl-aryl bond. The protecting group on the amino nitrogen of indoline I-7 is removed by treatment with an appropriate acid, such as trifluoroacetic acid, in an appropriate solvent, such as $CH_2Cl_2$, to yield amine I-8.

SCHEME 1

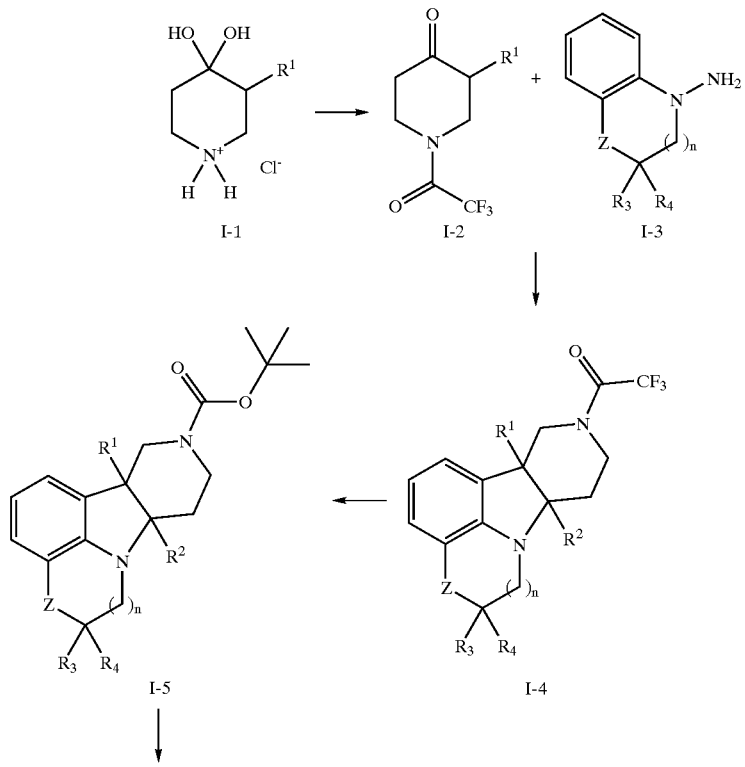

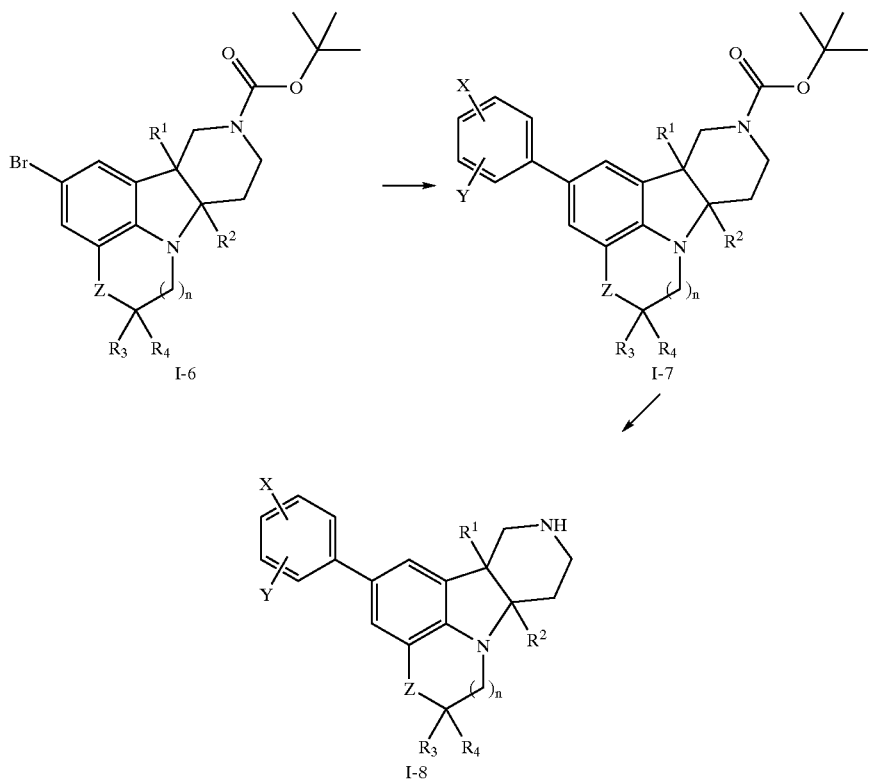

A substituted hydrazine hydrochloride II-1 and a γ-ketocarboxylic acid II-2 in an appropriate solvent, such as 2-propanol, at reflux are reacted to yield indole II-3 (Scheme 2). M W Bullock, S W Fox, J. Am. Chem. Soc. 73 5155–7 (1951). The indole II-3 is treated with an oxidant, such as singlet oxygen, followed by a mild reducing reagent, such as dimethyl sulfide, to prepare rearrangement product II-4, which is in turn treated with a base, such as 10% KOH in MeOH, to provide ketoacid II-5. M Ihara, K Noguchi, K Fukumoto, T Kamatani, Tetrahedron 41 2109–14 (1985). Ketoacid II-5 is condensed with an appropriate amine to yield amide II-6. A Couture, E Deniau, P Woisel, P Grandclaudon, J F Carpentier, Tetrahedron Lett. 37 3697–3700 (1996). Amide II-6 is converted to olefin II-7 by means of an intramolecular Wittig reaction and II-7 is in turn reduced by means of an appropriate reagent, such as $H_2$, Pd/C, to yield amide II-8. Amide II-8 is treated with a suitable reducing agent, such as LAH, to yield amine II-9. The benzyl protecting group of amine II-9 is removed under suitable conditions, such as $H_2$, Pd/C, and the resulting secondary amine is protected with an appropriate protecting group, such as the Boc group, under appropriate conditions, such as $(Boc)_2O$, 1N KOH, EtOAc, to yield indoline II-10. II-10 is converted to II-12 by essentially the same procedure as is previously described for the conversion of I-5 to I-8.

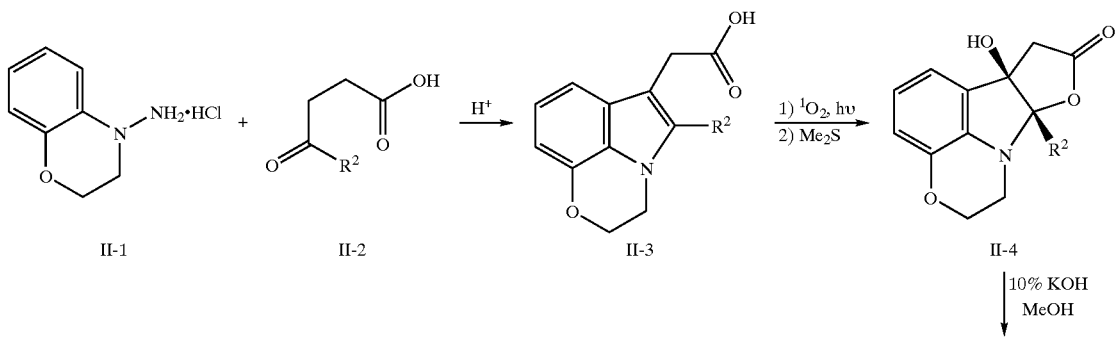

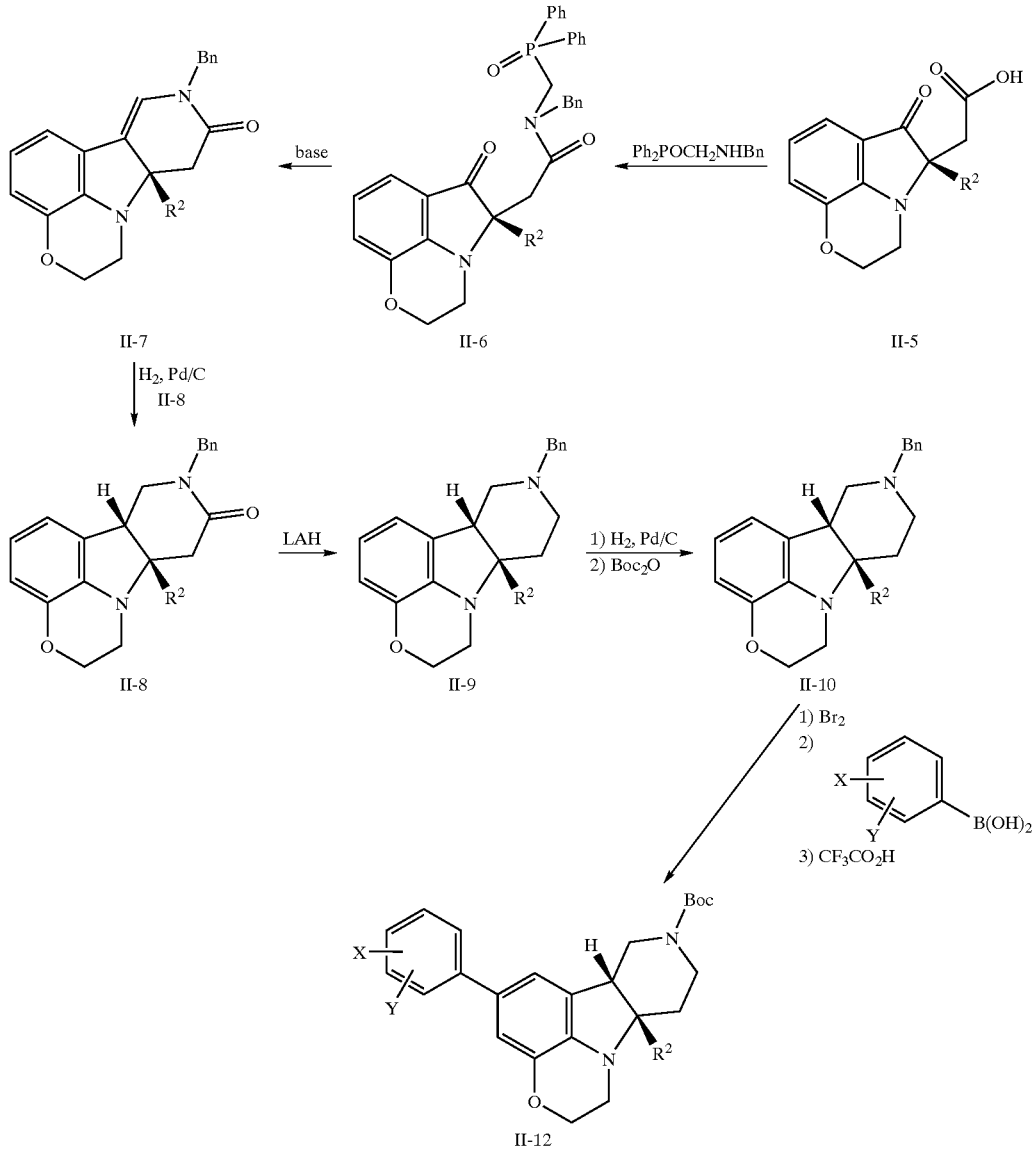

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of Formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of Formula (I) that act as either agonists or as antagonists of one or more 5-HT receptor subtypes. The compounds of the invention are 5-HT ligands, which typically displace>50% of a radiolabeled test ligand from one or more 5-HT receptor subtype at a concentration of 1 $\mu$M. The procedures used for testing such displacement are well known and would be readily available to one skilled in the art. For example, see L. W. Fitzgerald et al., *Mol. Pharmacol*, 2000, 57, 1, 75–81; and D. B. Wainscott, et al., *J. Pharmacol Exp Ther*, 1996, 276, 2, 720–727.

DESCRIPTION OF PREFERRED EMBODIMENTS

Preparation 1

Preparation of 1-Trifluoroacetyl-3-methylpiperidin-4-one

3-Methyl-4-piperidone hydrochloride (1.00 g, 6.68 mmol) was suspended in $CH_2Cl_2$ (50 mL) and stirred at room temperature under $N_2$. Pyridine (1.35 mL, 16.7 mmol) was added to the reaction mixture followed by trifluoroacetic anhydride (1.13 mL, 8.02 mmol). The reaction mixture was stirred at room temperature for 1.5 hours. The reaction mixture was diluted with $CH_2Cl_2$ (50 mL) and washed with 5% aqueous $NaHCO_3$ (1×25 mL), 10% citric acid (1×25 mL) and water (1×25 mL). The organic phase was dried over $Na_2SO_4$, filtered and concentrated to yield 1-trifluoroacetyl-3-methylpiperidin-4-one (1.33 g) in 95% yield. MS (ESI+) for $C_8H_{10}F_3NO_2$ m/z 210.1 $(M+H)^+$.

Preparation 2

Preparation of 8-Trifluoroacetyl-6b-methyl-1,2,6b,7,8,9,10,10a-octahydro[1,4]oxazino[2,3,4-hi]pyrido[4,3-b]indole 2,3-Dihydro-4H-1,4-benzoxazin-4-amine hydrochloride (0.0830 g, 0.444 mmol) and 1-trifluoroacetyl-3-methylpiperidin-4-one (0.0929 g, 0.444 mmol) were combined in 2-propanol (3.75 mL) and stirred at reflux for 3.75 hours under $N_2$. The reaction mixture was cooled to room temperature, $NaBH_4$ (0.0523 g, 1.38 mmol) was added and the reaction mixture was refluxed for 1 hour under $N_2$. The cooled reaction mixture was quenched with $CH_3OH$ (2 mL) and partitioned between $CH_2Cl_2$ and $H_2O$. The layers were separated and the aqueous layer was extracted with $CH_2Cl_2$. The combined $CH_2Cl_2$ extracts were washed with $H_2O$, dried over $Na_2SO_4$, filtered and concentrated to yield crude 8-trifluoroacetyl-6b-methyl-1,2,6b,7,8,9,10,10a-octahydro[1,4]oxazino[2,3,4-hi]pyrido[4,3-b]indole (0.130 g). MS (ESI+) for $C_{16}H_{17}F_3N_2O_2$ m/z 327.0 $(M+H)^+$.

Preparation 3

Preparation of tert-Butyl 6b-methyl-1,2,6b,9,10,10a-hexahydro[1,4]oxazino[2,3,4-hi]pyrido[4,3-b]indole-8(7H)-carboxylate 8-Trifluoroacetyl-6b-methyl-1,2,6b,7,8,9,10,10a-octahydro[1,4]oxazino[2,3,4-hi]pyrido[4,3-b]indole and NaOH (0.209 g, 5.23 mmol) were dissolved in a mixture of THF (5 mL) and $H_2O$ (5 mL). The resulting mixture was stirred vigorously for 4 hours. Di-tert-butyl dicarbonate (0.463 g, 2.12 mmol) was added in two separate portions and the reaction mixture was stirred at room temperature for 40 hours. The reaction mixture was concentrated and the residue was partitioned between EtOAc (25 mL) and $H_2O$ (25 mL). The layers were separated and the aqueous layer was extracted with EtOAc (25 mL). The combined organic layers were washed with brine (15 mL), dried over $MgSO_4$, filtered and concentrated to yield a crude product (0.168 g), which was purified by chromatography ($SiO_2$ 20 g, eluted with 1:1 heptane:$Et_2O$) tert-butyl 6b-methyl-1,2,6b,9,10,10a-hexahydro[1,4]-oxazino[2,3,4-hi]pyrido[4,3-b]indole-8(7H)-carboxylate (0.0841 g) in 57% overall yield from 2,3-dihydro-4H-1,4-benzoxazin-4-amine hydrochloride and 1-trifluoroacetyl-3-methylpiperidin-4-one. $^1$H NMR (500 MHz, $CD_3OD$) δ1.35(s, 3 H), 1.49(s, 9 H), 1.81–1.89(m,1 H), 1.93–1.98(m, 1 H), 2.70(ddd, J=11,10,3.3 Hz, 1 H), 2.80–3.06(br m, 1 H), 2.94(br s, 1 H), 3.11–3.22(br m, 1 H), 3.41(ddd,J=11.0,2.2,2.2 Hz, 1 H), 3.70–3.87(br m, 1 H), 3.90(br d, J=10.9 Hz, 1 H), 4.41(ddd,J=11,10,2.3 Hz, 1 H), 4.45(ddd,J=11,3,2 Hz, 1 H), 6.56(dd,J=5,4 Hz, 1 H), 6.66 (d,J=5 Hz, 1 H), 6.66(d,J=4 Hz, 1 H); MS (ESI+) for $C_{19}H_{26}N_2O_3$ m/z 331.0 $(M+H)^+$.

Using synthetic procedures similar to those described herein, the following compounds of Formula (II) can also be prepared.

tert-Butyl 6b-methyl-1,2,6b,9,10,10a-hexahydro[1,4]oxazino[2,3,4-hi]pyrido[4,3-b]indole-8(7H)-carboxylate;

tert-butyl-5-(2,4-dichlorophenyl)-10a-methyl-1,2,6b,7,8,9,10,10a-octahydro[1,4]oxazino[2,3,4-hi]pyrido[4,3-b]indole-8(7H)-carboxylate;

tert-butyl-5-(2,6-difluorophenyl)-10a-methyl-1,2,6b,7,8,9,10,10a-octahydro[1,4]oxazino[2,3,4-hi]pyrido[4,3-b]indole-8(H)-carboxylate;

tert-butyl-5-(2,4-dichlorophenyl)-10a-ethyl-1,2,6b,7,8,9,10,10a-octahydro[1,4]oxazino[2,3,4-hi]pyrido[4,3-b]indole-8(7H)-carboxylate;

tert-butyl-5-(2,6-difluorophenyl)-10a-ethyl-1,2,6b,7,8,9,10,10a-octahydro[1,4]oxazino[2,3,4-hi]pyrido[4,3-b]indole-8(7H)-carboxylate;

tert-butyl-5-(2,4-dichlorophenyl)-10a-methyl-1,2,6b,7,8,9,10,10a-octahydropyrido[4,3-b][1,4]thiazino[2,3,4-hi]indole-8(7H)-carboxylate;

tert-butyl-5-(2,6-difluorophenyl)-10a-methyl-1,2,6b,7,8,9,10,10a- octahydropyrido[4,3-b][1,4]thiazino[2,3,4-hi]indole-8(7H)-carboxylate;

tert-butyl-5-(2,4-dichlorophenyl)-10a-ethyl-1,2,6b,7,8,9,10,10a-octahydropyrido[4,3-b][1,4]thiazino[2,3,4-hi]indole-8(7H)-carboxlate; or tert-butyl-5-(2,6-difluorophenyl)-10a-ethyl-1,2,6b,7,8,9,10,10a- octahydropyrido[4,3-b][1,4]thiazino[2,3,4-hi]indole.

EXAMPLE 1

Preparation of 6b-Methyl-1,2,6b,7,8,9,10,10a-octahydro[1,4]oxazino[2,3,4-hi]pyrido[4,3-b]indole

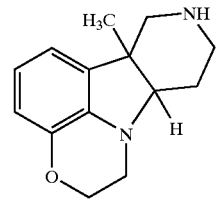

tert-Butyl 6b-methyl-1,2,6b,9,10,10a-hexahydro[1,4]-oxazino[2,3,4-hi]pyrido[4,3-b]indole-8(7H)-carboxylate (0.0711 g, 0.215 mmol) was dissolved in $CH_2Cl_2$ (2 mL). Trifluoroacetic acid (0.50 mL, 0.46 mmol) was added and the reaction mixture was stirred in a sealed reaction vessel for 4 hours at room temperature. The reaction mixture was cooled in an ice bath and 1N aqueous NaOH (15 mL) was added and the resulting mixture was extracted with $CH_2Cl_2$ (2×25 mL) and 25:1 $CH_2Cl_2$:$CH_3OH$ (1×26 mL). The combined organic extracts were dried over $Na_2SO_4$, filtered and concentrated to yield a crude product (0.0464 g), which was purified by chromatography ($SiO_2$ 10 g, eluted with 90:10:1 $CH_2Cl_2$:$CH_3OH$:concentrated aqueous $NH_4OH$) to yield 6b-methyl-1,2,6b,7,8,9,10,10a-octahydro[1,4]oxazino

[2,3,4-hi]pyrido[4,3-b]indole (0.0453 g) in 91% yield. $^1$H NMR (400 MHz, CD$_3$OD) δ1.42 (s, 3 H), 1.78–1.87 (m, 1 H), 1.90–1.96 (m, 1 H), 2.68 (ddd, J=10.8, 9.5, 3.5 Hz, 1 H), 2.71 (d, J=13.3 Hz, 1H), 2.74 (d, J=13.3 Hz, 1 H), 2.81–2.94 (m, 3 H) 3.40 (ddd, J=11.0, 2.1, 2.1 Hz, 1 H), 4.37–4.47 (m,2H), 6.53 (dd, J=7.5, 1.7 Hz, 1 H), 6.59–6.65 (m, 2 H); 1.96 (m, 1 H MS (ESI+) for C$_{14}$H$_{18}$N$_2$O m/z 231.1 (M+H)$^+$.

Using synthetic procedures similar to those described herein, the following compounds of Formula (I) can also be prepared.

5-(2,6-difluorophenyl)-10a-ethyl-1,2,6b,7,8,9,10,10a-octahydro[1,4]oxazino[2,3,4-hi]pyrido[4,3-b]indole

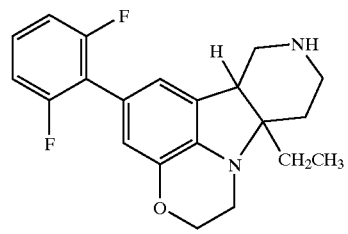

5-(2,4-dichlorophenyl)-10a-methyl-1,2,6b,7,8,9,10,10a-octahydro[1,4]oxazino[2,3,4-hi]pyrido[4,3-b]indole

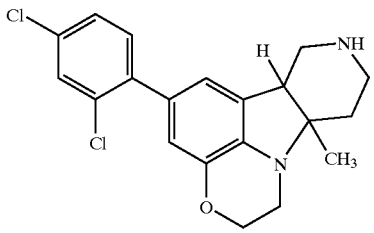

5-(2,4-dichlorophenyl)-10a-methyl-1,2,6b,7,8,9,10,10a-octahydropyrido[4,3-b][1,4]thiazino[2,3,4-hi]indole

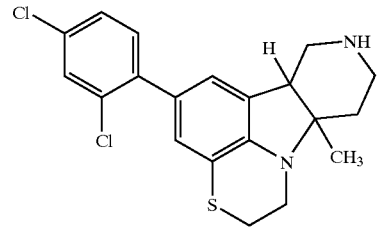

5-(2,6-difluorophenyl)-10a-methyl-1,2,6b,7,8,9,10,10a-octahydro[1,4]oxazino[2,3,4-hi]pyrido[4,3-b]indole

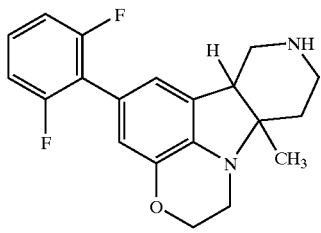

5-(2,6-difluorophenyl)-10a-methyl-1,2,6b,7,8,9,10,10a-octahydropyrido[4,3-b][1,4]thiazino[2,3,4-hi]indole

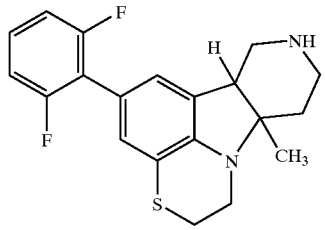

5-(2,4-dichlorophenyl)-10a-ethyl-1,2,6b,7,8,9,10,10a-octahydro[1,4]oxazino[2,3,4-hi]pyrido[4,3-b]indole

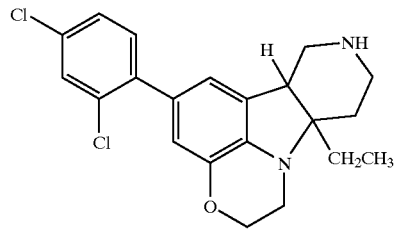

5-(2,4-dichlorophenyl)-10a-ethyl-1,2,6b,7,8,9,10,10a-octahydropyrido[4,3-b][1,4]thiazino[2,3,4-hi]indole

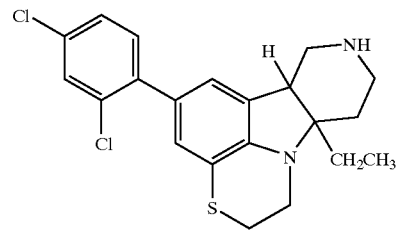

5-(2,6-difluorophenyl)-10a-ethyl-1,2,6b,7,8,9,10, 10a-octahydropyrido[4,3-b][1,4]thiazino[2,3,4-hi] indole

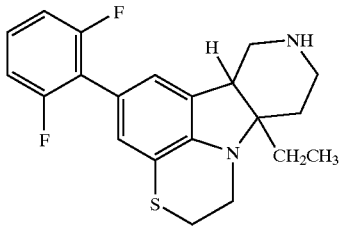

The invention has been described with reference to various specific and preferred embodiments and techniques. However, it should be understood that many variations and modifications may be made while remaining within the spirit and scope of the invention.

What is claimed is:

1. A compound of Formula (I):

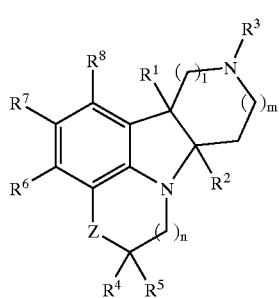

(I)

wherein Z is —O— or —S—;

l is 1 or 2;

m is 0, 1 or 2;

n is 1;

$R^1$ and $R^2$ are each independently hydrogen, $C_{1-6}$alkyl, $C_{3-6}$cycloalkyl, or $(C_{3-6}$cycloalkyl$)C_{1-6}$alkyl; provided that $R^1$ and $R^2$ are not both hydrogen;

$R^3$ is hydrogen or $C_{1-6}$alkyl;

$R^4$ and $R^5$ are independently hydrogen, $C_{1-6}$alkyl or aryl$C_{1-6}$alkylene;

$R^6$, $R^7$, and $R^8$ are independently hydrogen, fluoro, chloro, bromo, $CF_3$, —$OCF_3$, —$N(R^{10})_2$, $C_{1-6}$alkyl, $C_{1-6}$alkoxy, heteroaryl or aryl;

each $R^{10}$ is independently hydrogen, or —$C_{1-6}$alkyl;

wherein any $C_{1-6}$alkyl, $C_{1-6}$alkylene, or $C_{1-6}$alkoxy of $R^1$, $R^2$, $R^3$, $R^4$, $R^5$, $R^6$, $R^7$, $R^8$, $R^9$, and $R^{10}$ is optionally partially unsaturated;

wherein any heteroaryl or aryl is optionally substituted with one or two substituents independently selected from halo, —$CF_3$, —$OCF_3$, $C_{1-6}$alkoxy, —$N(R_{10})_2$, and $C_{1-6}$alkyl;

or a pharmaceutically acceptable salt thereof.

2. The compound of claim 1, wherein $R^1$ is hydrogen.

3. The compound of claim 1, wherein $R^1$ is $C_{1-6}$alkyl, $C_{3-6}$cycloalkyl, or $(C_{3-6}$cycloalkyl$)C_{1-6}$alkyl.

4. The compound of claim 1, wherein $R^1$ is $C_{2-6}$alkyl, $C_{3-6}$cycloalkyl, or $(C_{3-6}$cycloalkyl$)C_{1-6}$alkyl.

5. The compound of claim 1, wherein $R^1$ is $C_{3-6}$alkyl, $C_{3-6}$cycloalkyl, or $(C_{3-6}$cycloalkyl$)C_{1-6}$alkyl.

6. The compound of claim 1, wherein $R^1$ is methyl, ethyl, propyl, isopropyl, or cyclopropylmethyl.

7. The compound of claim 1, wherein $R^1$ is ethyl, propyl, isopropyl, or cyclopropylmethyl.

8. The compound of claim 1, wherein $R^1$ is propyl, isopropyl, or cyclopropylmethyl.

9. The compound of claim 1, wherein $R^2$ is hydrogen.

10. The compound of claim 1, wherein $R^2$ is $C_{1-6}$alkyl, $C_{3-6}$cycloalkyl, or $(C_{3-6}$cycloalkyl$)C_{1-6}$alkyl.

11. The compound of claim 1, wherein $R^2$ is $C_{2-6}$alkyl, $C_{3-6}$cycloalkyl, or $(C_{3-6}$cycloalkyl$)C_{1-6}$alkyl.

12. The compound of claim 1, wherein $R^2$ is $C_{3-6}$alkyl, $C_{3-6}$cycloalkyl, or $(C_{3-6}$cycloalkyl$)C_{1-6}$alkyl.

13. The compound of claim 1, wherein $R^2$ is methyl, ethyl, propyl, isopropyl, or cyclopropylmethyl.

14. The compound of claim 1, wherein $R^2$ is ethyl, propyl, isopropyl, or cyclopropylmethyl.

15. The compound of claim 1, wherein $R^2$ is propyl, isopropyl, or cyclopropylmethyl.

16. The compound of claim 10, wherein $R^1$ is hydrogen.

17. The compound of claim 1, wherein $R^1$ is $C_{2-3}$alkyl and $R^2$ is hydrogen, or $C_{2-6}$alkyl.

18. The compound of claim 1, wherein $R^1$ is hydrogen, or $C_{2-3}$alkyl; and $R^2$ is $C_{2-6}$alkyl.

19. The compound of claim 1, wherein $R^1$ is $C_{2-3}$alkyl and $R^2$ is $C_{2-6}$alkyl.

20. The compound of claim 1, wherein $R^1$ is ethyl or propyl and $R^2$ is ethyl, propyl or butyl.

21. The compound of claim 1, wherein $R^3$ is hydrogen.

22. The compound of claim 1, wherein $R^3$ is $C_{1-6}$alkyl.

23. The compound of claim 22, wherein $R^3$ is methyl, ethyl, propyl, or butyl.

24. The compound of claim 23, wherein $R^3$ is methyl or ethyl.

25. The compound of claim 1, wherein $R^4$ and $R^5$ are independently hydrogen, methyl, ethyl, propyl, butyl, 2-phenylethyl, or benzyl.

26. The compound of claim 25, wherein $R^4$ and $R^5$ are independently hydrogen, methyl, ethyl, propyl, or benzyl.

27. The compound of claim 25, wherein $R^4$ and are independently methyl, ethyl, or benzyl.

28. The compound of claim 1, wherein $R^6$, $R^7$, or $R^8$ is phenyl optionally substituted with one or two substituents independently selected from halo, —$CF_3$, —$OCF_3$, $C_{1-6}$alkoxy, —$N(R^{10})_2$, and $C_{1-6}$alkyl.

29. The compound of claim 28, wherein $R^6$, $R^7$, or $R^8$ is phenyl optionally substituted with one or two substituents independently selected from fluoro, chloro, bromo, —$CF_3$, —$OCF_3$, $C_{1-6}$alkoxy and —$N(R^{10})_2$.

30. The compound of claim 28, wherein $R^6$, $R^7$, or $R^8$ is phenyl optionally substituted with one or two substituents independently selected from fluoro, chloro, and bromo.

31. The compound of claim 28, wherein $R^6$ is 2,4-dichlorophenyl or 2,6-difluorophenyl.

32. The compound of claim 28, wherein $R^7$ is 2,4-dichlorophenyl or 2,6-difluorophenyl.

33. The compound of claim 28, wherein $R^8$ is 2,4-dichlorophenyl or 2,6-difluorophenyl.

34. The compound of claim 1 which is 6b-methyl-1,2,6b, 7,8,9,10,10a-octahydro [1,4]oxazino [2,3,4-hi]pyrido[4,3-b] indole; or a pharmaceutically acceptable salt thereof.

35. The compound of claim 1 which is 5-(2,4-dichlorophenyl)-10a-methyl-1,2,6b,7,8,9,10,10a-octahydro[1,4]oxazino[2,3,4-hi]pyrido[4,3-b]indole;

5-(2,6-difluorophenyl)-10a-methyl-1,2,6b,7,8,9,10,10a-octahydro[1,4]oxazino[2,3,4-hi]pyrido[4,3-b]indole;

5-(2,4-dichlorophenyl)-10a-ethyl-1,2,6b,7,8,9,10,10a-octahydro[1,4]oxazino[2,3,4-hi]pyrido[4,3-b]indole;

5-(2,6-difluorophenyl)-10a-ethyl-1,2,6b,7,8,9,10,10a-octahydro[1,4]oxazino[2,3,4-hi]pyrido[4,3-b]indole;

5-(2,4-dichlorophenyl)-10a-methyl-1,2,6b,7,8,9,10,10a-octahydropyrido[4,3-b][1,4]thiazino[2,3,4-hi]indole;

5-(2,6-difluorophenyl)-10a-methyl-1,2,6b,7,8,9,10,10a-octahydropyrido[4,3-b][1,4]thiazino[2,3,4-hi]indole;

5-(2,4-dichlorophenyl)-10a-ethyl-1,2,6b,7,8,9,10,10a-octahydropyrido[4,3-b][1,4]thiazino[2,3,4hi]indole; or 5-(2,6-difluorophenyl)-10a-ethyl-1,2,6b,7,8,9,10,10a-octahydropyrido[4,3-b][1,4]thiazino[2,3,4-hi]indole;

or a pharmaceutically acceptable salt thereof.

36. A pharmaceutical composition comprising a compound of claim 1 and a pharmaceutically acceptable excipient.

37. A method for treating a CNS disease or condition in a mammal in need thereof wherein the 5-HT$_{2C}$ receptor is implicated and modulation of 5-HT$_{2C}$ function is desired, and wherein the CNS disease or condition is selected from the group consisting of anxiety, depression, obsessive compulsive disorder, panic disorder, phobias, psychiatric syndrome, obesity and migraine headache, comprising administering a therapeutically effective amount of a compound of claim 1 to the mammal.

38. A compound of Formula (II):

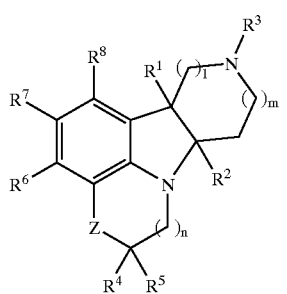

(II)

wherein Z is —O— or —S—;

l is 1 or 2;

m is 0, 1 or 2;

n is 1;

$R^1$ and $R^2$ are each independently hydrogen, $C_{1-6}$alkyl, $C_{3-6}$cycloalkyl, or $(C_{3-6}$cycloalkyl$)C_{1-6}$alkyl; provided that $R^1$ and $R^2$ are not both hydrogen;

$R^3$ is —C(O)-aryl, —C(O)-heteroaryl, —C(O)—$C_{1-6}$alkyl, —C(O)—$C_{1-6}$haloalkyl, —C(O)O—$C_{1-6}$alkyl, or —C(O)O—$C_{1-6}$haloalkyl, where aryl or heteroaryl is optionally substituted with one or two halo, —CF$_3$, —OCF$_3$, $C_{1-6}$alkoxy, —N(R$^{10}$)$_2$, or —$C_{1-6}$alkyl;

$R^4$ and $R^5$ are independently hydrogen, $C_{1-6}$alkyl or aryl$C_{1-6}$alkylene;

$R^6$, $R^7$, and $R^8$ are independently hydrogen, fluoro, chloro, bromo, CF$_3$, —OCF$_3$, —N(R$^{10}$)$_2$, $C_{1-6}$alkyl, $C_{1-6}$alkoxy, heteroaryl or aryl;

each R$^{10}$ is independently hydrogen, or —$C_{1-6}$alkyl;

wherein any $C_{1-6}$alkyl, $C_{1-6}$alkylene, or $C_{1-6}$alkoxy of $R^1$, $R^2$, $R^3$, $R^4$, $R^5$, $R^6$, $R^7$, $R^8$, and R$^{10}$ is optionally partially unsaturated;

wherein any heteroaryl or aryl is optionally substituted with one or two substituents independently selected from halo, —CF$_3$, —OCF$_3$, $C_{1-6}$alkoxy, —N(R$^{10}$)$_2$, and $C_{1-6}$alkyl.

39. The compound of claim 38 which is tert-Butyl 6b-methyl-1,2,6b, 9,10,10a-hexahydro[1,4]oxazino [2,3,4-hi]pyrido[4,3-b]indole-8(7H)-carboxylate;

tert-butyl-5-(2,4-dichlorophenyl)-10a-methyl-1,2,6b,7,8,9,10,10a-octahydro[1,4]oxazino[2,3,4-hi]pyrido[4,3-b]indole-8(7H)-carboxylate;

tert-butyl-5-(2,6-difluorophenyl)-10a-methyl-1,2,6b,7,8,9,10,10a-octahydro[1,4]oxazino[2,3,4-hi]pyrido[4,3-b]indole-8(H)-carboxylate;

tert-butyl-5-(2,4-dichlorophenyl)-10a-ethyl-1,2,6b,7,8,9,10,10a-octahydro[1,4]oxazino[2,3,4-hi]pyrido[4,3-b]indole-8(7H)-carboxylate;

tert-butyl-5-(2,6-difluorophenyl)-10a-ethyl-1,2,6b,7,8,9,10,10a-octahydro[1,4]oxazino[2,3,4-hi]pyrido[4,3-b]indole-8(7H)-carboxylate;

tert-butyl-5-(2,4-dichlorophenyl)-10a-methyl-1,2,6b,7,8,9,10,10a-octahydropyrido[4,3-b][1,4]thiazino[2,3,4-hi]indole-8(7H)-carboxylate;

tert-butyl-5-(2,6-difluorophenyl)-10a-methyl-1,2,6b,7,8,9,10,10a-octahydropyrido[4,3-b][1,4]thiazino[2,3,4-hi]indole-8(7H)-carboxylate;

tert-butyl-5-(2,4-dichlorophenyl)-10a-ethyl-1,2,6b,7,8,9,10,10a-octahydropyrido[4,3-b][1,4]thiazino[2,3,4-hi]indole-8(7H)-carboxlate; or tert-butyl-5-(2,6-difluorophenyl)-10a-ethyl-1,2,6b,7,8,9,10,10a-octahydropyrido[4,3-b][1,4]thiazino[2,3,4-hi]indole.

40. The compound of claim 39, which is tert-butyl 6b-methyl-1,2,6b,9,10,10a-hexahydro[1,4]oxazino[2,3,4-hi]pyrido[4,3-b]indole-8(7H)-carboxylate.

* * * * *